United States Patent
Mostafá et al.

(10) Patent No.: US 11,939,623 B2
(45) Date of Patent: Mar. 26, 2024

(54) METHODS AND REAGENTS FOR NUCLEIC ACIDS DETECTION

(71) Applicant: GenoSUR, LLC, Miami, FL (US)

(72) Inventors: Matías Ricardo Gutiérrez Mostafá, Ñuñoa Santiago (CL); Chantal Loretto Márquez Badilla, Ñuñoa Santiago (CL); Ana Cecilia Morán, Ñuñoa Santiago (CL)

(73) Assignee: GenoSUR, LLC, Miami, FL (US)

( * ) Notice: Subject to any disclaimer, the term of this patent is extended or adjusted under 35 U.S.C. 154(b) by 0 days.

(21) Appl. No.: 17/020,804

(22) Filed: Sep. 14, 2020

(65) Prior Publication Data

US 2021/0363567 A1    Nov. 25, 2021

Related U.S. Application Data

(60) Provisional application No. 63/026,728, filed on May 19, 2020.

(51) Int. Cl.
| | | |
|---|---|---|
| *C12Q 1/6806* | (2018.01) | |
| *C12Q 1/6844* | (2018.01) | |
| *C12Q 1/6851* | (2018.01) | |
| *C12Q 1/686* | (2018.01) | |
| *C12Q 1/70* | (2006.01) | |

(52) U.S. Cl.
CPC ......... *C12Q 1/6806* (2013.01); *C12Q 1/6844* (2013.01); *C12Q 1/6851* (2013.01); *C12Q 1/686* (2013.01); *C12Q 1/70* (2013.01)

(58) Field of Classification Search
CPC .. C12Q 1/6806; C12Q 1/6844; C12Q 1/6851; C12Q 1/686; C12Q 1/70
See application file for complete search history.

(56) References Cited

U.S. PATENT DOCUMENTS

2018/0258419 A1*  9/2018  Fischer .................. C12Q 1/686

OTHER PUBLICATIONS

Nowotny et al., Euro. Surveill., 19(16): pii-20781, 1-5 (Year: 2014).*
Qiagen., Qiagen OneStep RT-PCR Handbook, pp. 1-44, October (Year: 2012).*
Petrosillo et al., Clinical Microbiology and Infection 26, pp. 729-734, Mar. 28, (Year: 2020).*
Chan et al., Journal of Clinical Microbiology, vol. 58, issue 5, e00310-20, pp. 1-10, published Apr. 23, (Year: 2020).*

* cited by examiner

*Primary Examiner* — Cynthia B Wilder
(74) *Attorney, Agent, or Firm* — Hailey Law LLC; Xavier L. Hailey

(57) ABSTRACT

A method of use and reagent kit for nucleic acid stabilization and room temperature transport of SARS-CoV-2 and other respiratory viruses, followed by rapid identification are disclosed. Using the methods and compositions herein, molecular diagnostics or detection of SARS-CoV-2 and other respiratory viruses from the biological sample is performed without extraction or purification of viral DNA or RNA.

14 Claims, 10 Drawing Sheets

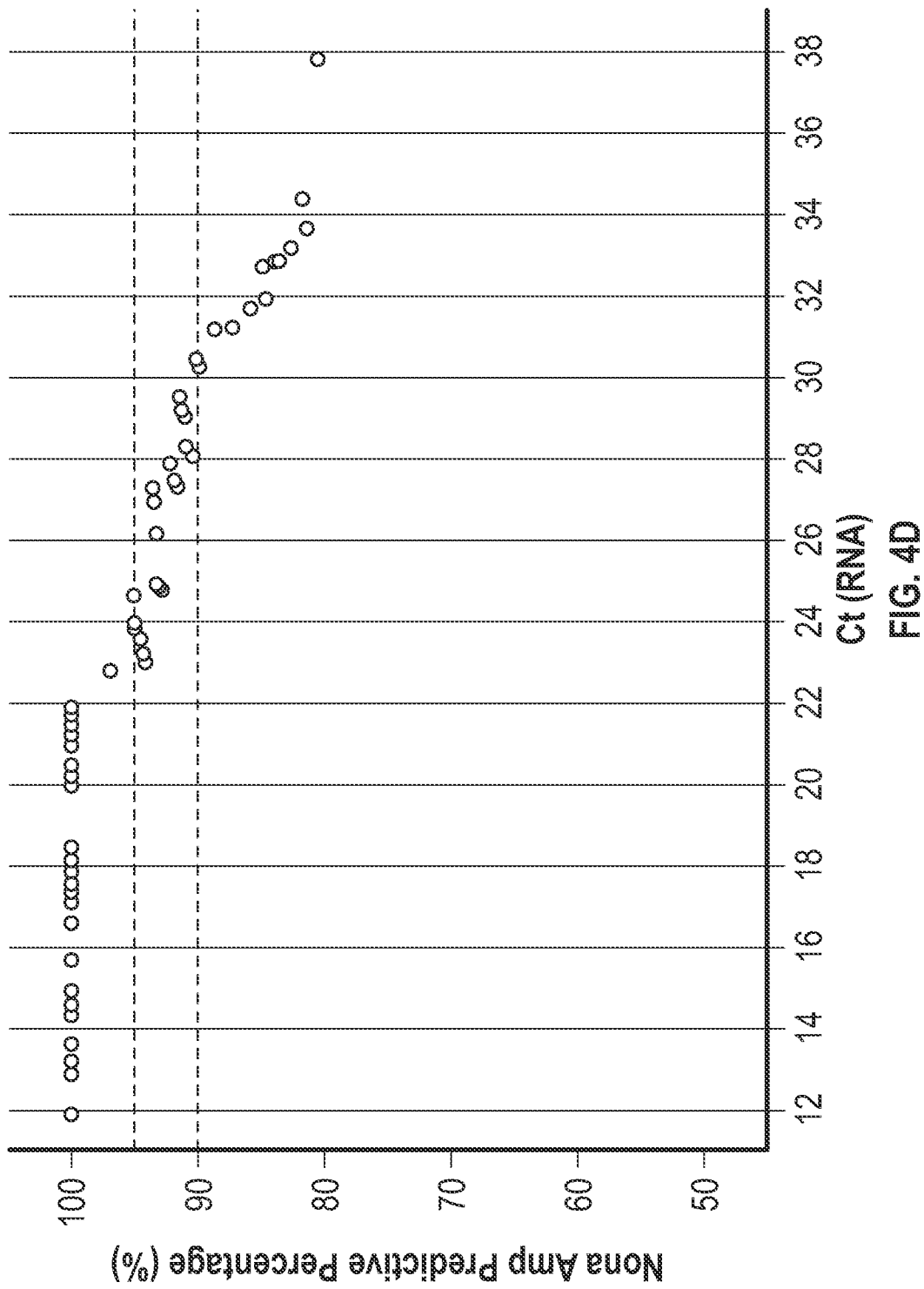

METHODS AND REAGENTS FOR NUCLEIC ACIDS DETECTION

CROSS-REFERENCE TO RELATED APPLICATIONS

This application claims benefit of priority to U.S. provisional application No. 63/026,728 filed on May 19, 2020, which is incorporated by reference herein.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

FIELD

The present invention relates generally to systems and methods that allow for direct detection of nucleic acids from samples that have been collected in stabilization reagents. More particularly, the present invention concerns methods and compositions that allow a user to skip the nucleic acid purification step and therefore perform nucleic acid detection directly from the stabilized sample, conserving the validity of the detection technique (RT-qPCR, qPCR, PCR, sequencing, hybridization, among others).

INTRODUCTION

Detection of nucleic acids and/or molecular diagnostics for research and/or diagnostics purposes, usually involves the following steps: (1) collection of a biological sample; (2) stabilization of the biological sample; (3) lysis of cell or viral particles; (4) purification of nucleic acids, and (5) detection of DNA or RNA using techniques such as PCR, RT-PCR, qPCR, RT-qPCR, sequencing, hybridization, and other nucleic acid analysis methods.

Viral pandemic attributed to SARS-CoV-2 imposes a challenge to the world's capacity to perform molecular diagnostics of the SARS-CoV-2. The supply of RNA extraction reagents is not plentiful. The lack of supply of RNA extract agents is a bottleneck for performing SARS-CoV-2 diagnostics, which renders laboratories ineffective at performing diagnostics. Further, viral pandemic outbreaks require fast deployment of a large quantity of diagnostics to identify infected individuals. The infected individuals can be subsequently isolated and thereby containing the spread of the virus.

In addition to supply shortage, the purification of nucleic acids is a laborious and time consuming step of the molecular diagnostics workflow. Furthermore, nucleic acid purification involves high manipulation, which may lead to sample degradation and reduced sensitivity. By virtue of sample degradation and reduced sensitivity, the efficacy and limit of detection of the molecular diagnosis are reduced.

SUMMARY

The present invention comprises a reagent and methods configured to make a stabilized sample's nucleic acids suitable for detection and/or analysis without requiring a nucleic acid purification step.

It is known in the art that different stabilization solutions contain different molecules that inhibit molecular detection and/or analysis techniques. In a preferred embodiment, the present invention comprises different reagents to antagonize the effect of PCR inhibitors of enzymatic reactions and to increase the availability of the nucleic acids.

In view of the foregoing disadvantages inherent in the art, the present invention relates to compositions and methods that allow for direct detection of nucleic acids from samples that have been collected in stabilization reagents. More specifically, disclosed here are additives for nucleic acid amplification reagents (e.g., mastermix additives (M-reagents)) and diluent of biological samples (e.g., sample diluents (S-reagents)) in transport solution from which nucleic acids can be amplified without the need for the nucleic acid purification process, thus optimizing the molecular diagnostics and clinical research applications.

In accordance with one aspect, a method is provided for detecting a pathogen in a biological sample. The method involves: stabilizing the biological sample and mixing the stabilized biological sample with an activating solution. The biological sample comprises a detectable polynucleotide. The activating solution comprises a buffered-based solution. PCR amplification of the mixture to amplify the detectable polynucleotide, thereby providing for the detection of the pathogen in the biological sample.

In accordance with a further aspect, a method for detecting a pathogen in a biological sample, the method comprising:
  (a) obtaining a stabilized sample, the stabilized sample comprising the biological sample and a transport solution, wherein the transport solution comprises a chaotropic agent and a chelating agent, and wherein the transport solution stabilizes a nucleic acid molecule of the pathogen in the stabilized sample at room temperature;
  (b) without prior extraction of the nucleic acid molecule present in the stabilized biological sample, mixing the stabilized sample with an activating solution, the activating solution comprising a buffer having pH from 6.8 to 8.2;
  (c) adding an amplification solution, the amplification solution comprising a non-ionic surfactant at a concentration of 0.5 to 5 percent (vol./vol.), to a DNA polymerase enzyme and, optionally, a reverse transcriptase enzyme, a DNA polymerase buffer, and a primer set specific for the nucleic acid molecule of the pathogen to form an amplification reaction mixture;
  (d) adding the stabilized and activated sample to the amplification reaction mixture;
  (e) subjecting the amplification reaction mixture to a polymerase chain reaction (PCR), wherein the PCR amplifies the nucleic acid molecule;
  (f) detecting the pathogen in the biological sample when a signal generated in the polymerase chain reaction surpasses a threshold signal for the polymerase chain reaction.

In accordance with a further aspect, the nucleic acid molecule is a ribonucleic acid (RNA) and a corresponding DNA molecule is produced from the RNA by a reverse transcriptase enzyme prior to or simultaneously with the polymerase chain reaction.

In accordance with a further aspect, the polymerase chain reaction is an RT-PCR, RT-qPCR or one-step RT-qPCR.

In accordance with a further aspect, the non-ionic surfactant in the amplification solution is at a concentration of 0.5 to 5 percent (vol./vol.) and is selected from the following group: NP-40 (CAS Number: 2315-61-9, 2-[2-[4-(2,4,4-trimethylpentan-2-yl)phenoxy]ethoxy]ethanol), Nonidet® P-40 (CAS Number: 26027-38-3; IUPAC: Octylphenoxypolyethoxyethanol), NP-40® substitutes, Tween® 20 (CAS Number: 9005-64-5; IUPAC: Polyoxyethylene (20) sorbitan monolaurate) Tween® 80 (CAS Number: 9005-65-6, IUPAC: Polyoxyethylene (80) sorbitan monooleate), Triton® X-100 (CAS Number: 9002-93-1; IUPAC: 2-[4-(2,4,4-trimethylpentan-2-yl)phenoxy]ethanol)

In accordance with a further aspect, the amplification solution further contains at least one nucleic-acid amplification enhancing agent.

In accordance with a further aspect, the at least one nucleic-acid amplification enhancing agent is one of the following: bovine serum albumin (BSA), dimethyl sulfoxide (DMSO), glycine, trehalose, polyethylene glycol (PEG), trimethylglycine (betaine), dNTPs, tetramethylene (TM) sulfone, TM sulfoxide, formamide, glycerol, tetramethylammonium (TMA) chloride, TMA oxalate, ammonium sulfate, acetamide, and 2-pyrrolidone.

In accordance with a further aspect, the nucleic-acid amplification enhancing agent is BSA at a concentration of 0.3 to 3 percent (vol./vol.).

In accordance with a further aspect, the nucleic-acid amplification enhancing agent is DMSO at a concentration of 0.5 to 5 percent (vol./vol.).

In accordance with a further aspect, the nucleic-acid amplification enhancing agent is dNTPs at a concentration of 50 to 500 uM.

In accordance with a further aspect, the nucleic-acid amplification enhancing agent is glycerol at a concentration of 0.5 to 5 percent (vol./vol.).

In accordance with a further aspect, the chaotropic agent in the transport solution is selected from the following group: guanidine hydrochloride, guanidine thiocyanate, potassium thiocyanate, sodium thiocyanate, and urea.

In accordance with a further aspect, the chaotropic agent in the transport solution is guanidine hydrochloride at a concentration of 0.5M to 2M.

In accordance with a further aspect, the chaotropic agent in the transport solution is sodium thiocyanate at a concentration of 0.5M to 6M.

In accordance with a further aspect, the chaotropic agent in the transport solution is guanidine thiocyanate at a concentration of 0.5M to 6M.

In accordance with a further aspect, the chelating agent in the transport solution is selected from the following group: diethylenetriaminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, nitrilotriacetic acid (NTA).

In accordance with a further aspect, the chelating agent in the transport solution is EDTA at a concentration of 20 mM to 60 mM.

In accordance with a further aspect, the chelating agent in the transport solution is EGTA at a concentration of 20 mM to 60 mM.

In accordance with a further aspect, the transport solution may further comprise a buffer having pH from 7.0 to 9.5, a reducing agent and a detergent, wherein the reducing agent is selected from the following group: 2-mercaptoethanol, thiosulfate, tris-(2-carboxyethyl) phosphine (TCEP), dithiothreitol, dithioerythritol, and the detergent is selected from the following group: Triton® X-100 (CAS Number: 9002-93-1; IUPAC: 2-[4-(2,4,4-trimethylpentan-2-yl)phenoxy]ethanol), Tween® 20 (CAS Number: 9005-64-5; IUPAC: Polyoxyethylene (20) sorbitan monolaurate), Tween® 80 (CAS Number: 9005-65-6, IUPAC: Polyoxyethylene (80) sorbitan monooleate), Nonidet® P-40 (CAS Number: 26027-38-3; IUPAC: Octylphenoxypolyethoxyethanol), Brij® 35 (CAS Number: 9002-92-0, IUPAC: Polyethylene glycol lauryl ether), an ethoxylated amine detergent, an alkylbenzene sulfonate detergent, sodium dodecyl sulfate (SDS).

In accordance with a further aspect, the transport solution may further comprise a Tris-HCL buffer having pH from 7.0 to 9.5 at a concentration of 50 mM to 150 mM.

In accordance with a further aspect, the pathogen is SARS-CoV-2.

In accordance with a further aspect, the activating solution comprises a Tris-HCL buffer having pH from 6.8 to 8.2 at a concentration of 5 mM to 20 mM; and the stabilized sample is diluted with the activating solution by a factor of 50, or by a factor of 100, or by a factor of 200.

In accordance with a further aspect, the activating solution comprises one of the following buffers having pH from 6.8 to 8.2: phosphate buffer, HEPES buffer (2-[4-(2-hydroxyethyl)piperazin-1-yl]ethanesulfonic acid), MOPS buffer (3-morpholinopropane-1-sulfonic acid), MES buffer (2-(N-morpholino)ethanesulfonic acid), Borate buffer.

In accordance with a further aspect, a reagent kit for detecting a pathogen in a biological sample is provided, the kit comprising:
  (a) a transport solution comprising a chaotropic agent and a chelating agent, wherein the transport solution stabilizes a nucleic acid molecule of the pathogen at room temperature for at least 48 hours;
  (b) an activating solution comprising a buffer having pH from 6.8 to 8.2;
  (c) an amplification solution comprising a non-ionic surfactant at a concentration of 0.5 to 5 percent (vol./vol.) and at least one nucleic-acid amplification enhancing agent.

In accordance with a further aspect, the kit further comprising a swab for transferring the sample to at least one tube and an instruction manual.

In accordance with a further aspect, the transport solution stabilizes a nucleic acid molecule of the pathogen at room temperature for at least 7 days.

In accordance with a further aspect, the at least one nucleic-acid amplification enhancing agent is one of the following: bovine serum albumin (BSA), dimethyl sulfoxide (DMSO), glycine, trehalose, polyethylene glycol (PEG), trimethylglycine (betaine), dNTPs, tetramethylene (TM) sulfone, TM sulfoxide, formamide, glycerol, tetramethylammonium (TMA) chloride, TMA oxalate, ammonium sulfate, acetamide, and 2-pyrrolidone; the chaotropic agent in the transport solution is selected from the following group: guanidine hydrochloride, guanidine thiocyanate, potassium thiocyanate, sodium thiocyanate, urea; the chelating agent in the transport solution is selected from the following group: diethylenetriaminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2- hydroxyethyl)ethylenediamine-N,N',N'-triacetic acid, nitrilotriacetic acid (NTA) and the non ionic surfactant in the amplification solution is at a concentration of 0.5 to 5 percent (vol./vol.) and is selected from the following group: NP-40 (CAS Number: 2315-61-9, 2-[2-[4-(2,4,4-trimethylpentan-2-yl)phenoxy]ethoxy]ethanol) Nonidet® P-40 (CAS Number: 26027-38-3, Octylphenoxypolyethoxyethano), NP-40® substitutes, Tween® 20 (CAS Number: 9005-64-5; IUPAC: Polyoxyethylene (20) sorbitan monolaurate), Tween® 80 (CAS Number: 9005-65-6, IUPAC: Polyoxyethylene (80) sorbitan monooleate), Triton® X-100 (CAS Number: 9002-93-1; IUPAC: 2-[4-(2,4,4-trimethylpentan-2-yl)phenoxy]ethanol).

In accordance with a further aspect, the activating solution comprises a Tris-HCL buffer having pH from 6.8 to 8.2 at a concentration of 5 mM to 20 mM; the nucleic-acid amplification enhancing agent is DMSO at a concentration of 0.5 to 5 percent (vol./vol.); the chaotropic agent in the transport solution is guanidine thiocyanate at a concentration of 0.5M to 6M, and the chelating agent is EDTA at a concentration of 20 mM to 60 mM.

In accordance with a further aspect, the transport solution further comprising a Tris-HCL buffer having pH from 8.5 to 9.5 at a concentration of 50 mM to 150 mM, a reducing agent and a detergent, wherein the reducing agent is selected from the following group: 2-mercaptoethanol, thiosulfate, tris-(2-carboxyethyl) phosphine (TCEP), dithiothreitol, dithioerythritol, and the detergent is selected from the following group: Triton® X-100 (CAS Number: 9002-93-1; IUPAC: 2-[4-(2,4,4-trimethylpentan-2-yl)phenoxy]ethanol), Tween® 20 (CAS Number: 9005-64-5: IUPAC: Polyoxyethylene (20) sorbitan monolaurate), Tween® 80 (CAS Number: 9005-65-6, IUPAC: Polyoxyethylene (80) sorbitan monooleate), Nonidet® P-40 (CAS Number: 26027-38-3; IUPAC: Octylphenoxypolyethoxyethanol), Brij® 35 (CAS Number: 9002-92-0, IUPAC: Polyethylene glycol lauryl ether), an ethoxylated amine detergent, an alkylbenzene sulfonate detergent, sodium dodecyl sulfate (SDS).

In another aspect, stabilizing the biological sample involves contacting the biological sample with a transport solution.

In another aspect, the amplification solution sequesters surfactants in the activating solution into micelles, thereby releasing the detectable polynucleotide.

In another aspect, PCR inhibitors are counteracted with quenching agents.

In another aspect, a predetermined amount of biological sample is mixed with a buffered transport solution.

In another aspect, the biological sample comprises: blood, urine, feces, serum, aerosol fluid, plasma, lymph, cerebrospinal fluid, saliva, mucosal secretion, vaginal fluid, ascites fluid, pleural fluid, pericardial fluid, peritoneal fluid, abdominal fluid, cell culture medium, organ culture medium, buccal cells, bacteria, viruses, yeast cells, lipids, proteins, homogenates, or extracts.

In another aspect, the biological sample in transport solution is diluted by a factor of 50, by factor of 100 or by factor of 200 by an activating solution before PCR amplification.

In another aspect, the quenching agent is a monovalent, divalent, or polyvalent cation.

In another aspect, a kit is provided for sampling, genome stabilization, pathogen inactivation and room temperature transport of SARS-CoV-2 and other respiratory viruses. The kit includes a swab for transferring a sample to a plurality of tubes and a well for housing each tube. Each tube contains a transport solution for containing a sample. Each sample is mixed with a surfactant-based solution and a PCR mix. The well is sent to a thermocycler.

BRIEF DESCRIPTION OF THE DRAWINGS

Those of skill in the art will understand that the drawings, described below, are for illustrative purposes only. The drawings are not intended to limit the scope of the present teachings in any way.

FIG. 2A—Example of amplification curves obtained with purified RNA (black curves) or from direct samples with Nona Amp® (grey curves). FIG. 2B—Correlation of Ct obtained from the same samples using Nona Amp® (grey) and with purified RNA (black). FIG. 2C—Difference of Ct obtained directly from the sample with Nona Amp® and with purified RNA for each sample. Bar represents the mean±SD and each dot corresponds to an individual data point. FIG. 2D Nona Amp® predictive percentage against Ct obtained with purified RNA. Reactions were performed on Rotor-Gene Q Real time PCR (Qiagen). Nona Amp® Ct values were obtained using a threshold of 0.07. RNA extraction was done using the SV Total RNA Isolation System (#Z3105, Promega). Ct from purified RNA was obtained using the TaqMan 2019-nCoV Assay Kit v1 detection kit (#A47532) with the TaqPath 1-Step RT-qPCR Master Mix, CG (#A15300), or with the LightMix® Modular Wuhan CoV RdRP-gene kit (Cat.-No. 53-0777-96, Roche) with the Roche LightCycler® Multiplex RNA Virus Master kit (Cat.-No. 06 754 155 001, Roche).

FIG. 3A—Example of amplification curves obtained with purified RNA (black curves) or from direct samples with Nona Amp (grey curves). FIG. 3B—Correlation of Ct obtained from the same samples using Nona Amp® (grey) and with purified RNA (black). Samples that were not detected with the direct method are shown in light-grey next to RNA data. FIG. 3C—Difference of Ct obtained directly from the sample with Nona Amp and with purified RNA for each sample. Bars represent the mean±SD and each dot corresponds to an individual data point. FIG. 3D—Nona Amp predictive percentage against Ct obtained with purified RNA for the three assayed viral RNAs. Ct were obtained using a threshold of 0.04. Reactions were performed on Rotor-Gene Q Real time PCR (Qiagen). RNA extraction was done using the Total RNA Purification Kit (#17200 Norgen) or SV Total RNA Isolation System (#Z3105, Promega). Ct from purified RNA was obtained using the TaqMan 2019-nCoV Assay Kit v1 detection kit (#A47532) with the TaqPath 1-Step RT-qPCR Master Mix, CG (#A15300), or with the LightMix® Modular Wuhan CoV RdRP-gene kit (Cat.-No. 53-0777-96, Roche) with the Roche LightCycler® Multiplex RNA Virus Master kit (Cat.-No. 06 754 155 001, Roche).

FIG. 4A-FIG. 4D. Nona Amp® allows SARS-CoV-2 detection directly from nasopharyngeal swab samples. Nasopharyngeal swab samples preserved in DNA/RNA Shield™ transport solution (N=72) were subjected to RT-qPCR to detect SARS-CoV-2 RdRp messenger RNA using the LightMix® Modular Wuhan CoV RdRP-gene kit (Cat.-No. 53-0777-96, Roche) with the Roche LightCycler® Multiplex RNA Virus Master kit (Cat.-No. 06 754 155 001, Roche). FIG. 4A—Example of amplification curves obtained with purified RNA (black curves) or from direct samples with Nona Amp (grey curves) or without Nona Amp (light-grey curves). FIG. 4B—Correlation of Ct obtained from the same samples using Nona Amp® (grey) and with purified RNA (black). Samples that were not detected with the direct method are shown next to RNA data. FIG. 4C—Difference of Ct obtained directly from the sample with Nona Amp and with purified RNA for each sample. Bars represent the mean±SD and each dot corresponds to an individual data point. FIG. 4D—Nona Amp predictive percentage against Ct obtained with purified RNA. Ct were obtained using a threshold of 0.06. Reactions were performed on Rotor-Gene Q Real time PCR (Qiagen). RNA extraction was done using the Total RNA Purification Kit (#17200 Norgen) or SV Total RNA Isolation System (#Z3105, Promega). Ct from purified RNA was obtained using the TaqMan 2019-nCoV Assay Kit v1 detection kit (#A47532) with the TaqPath 1-Step RT-qPCR Master Mix, CG (#A15300), or with the LightMix® Modular Wuhan CoV RdRP-gene kit (Cat.-No. 53-0777-96, Roche) with the Roche LightCycler® Multiplex RNA Virus Master kit (Cat.-No. 06 754 155 001, Roche).

FIG. 5A Example of amplification curves obtained with purified RNA (black curves) or from direct samples with Nona Amp® (grey curves). FIG. 5B Correlation of Ct obtained from the same samples using Nona Amp® (grey) and with purified RNA (black). Reactions were performed on Rotor-Gene Q Real time PCR (Qiagen). Ct values were obtained using a threshold of 0.04. RNA extraction was done using the SV Total RNA Isolation System (#Z3105, Promega).

DETAILED DESCRIPTION

Abbreviations and Definitions

Figure 1:
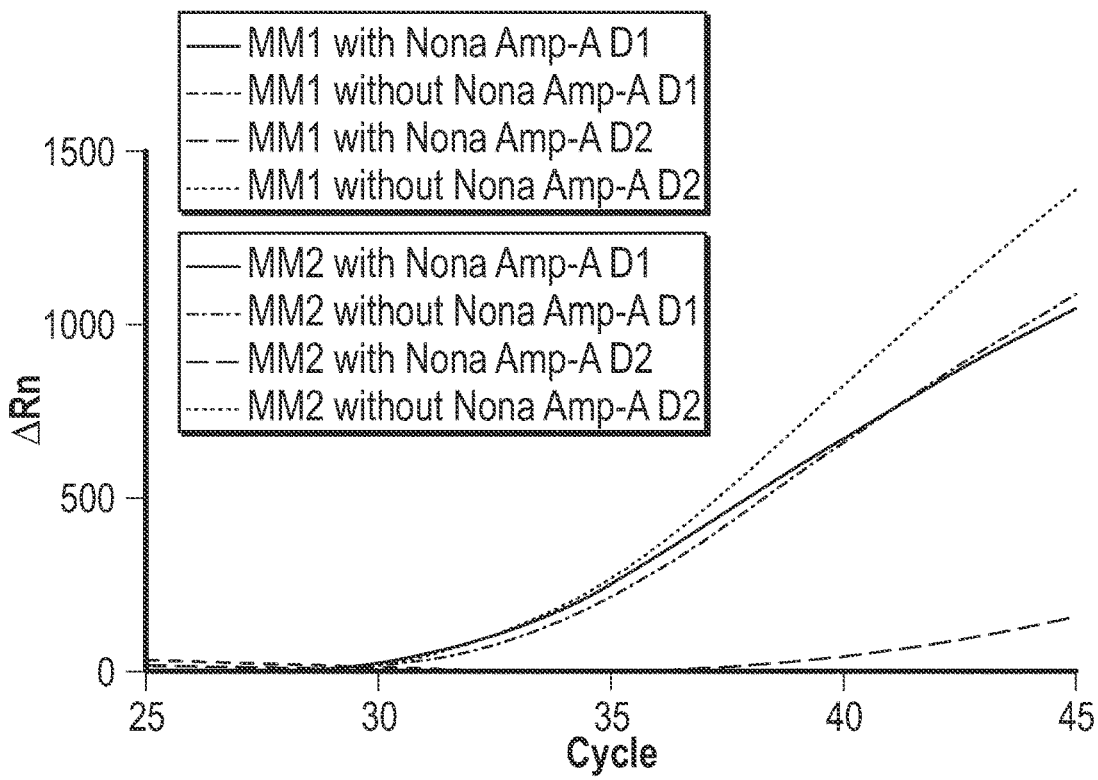
FIG. 1. Nona Amp A allows RT-qPCR detection of the RNAse P messenger RNA from a direct human tissue sample preserved in a nucleic acid transport solution without the RNA extraction step. Two RT-qPCR mastermix were tested, Brilliant III Ultra-Fast QRT-PCR Master Mix (MM1, Agilent #60884) and RT-qPCR Master Mix TaqMan™ Fast Virus 1-Step (MM2, Thermofisher #4444436) at two different sample dilutions (D1, 1:50 and D2, 1:100).

Recombinant: As used herein, the term "recombinant" refers to a nucleic acid molecule made by an artificial combination of two otherwise separated segments of sequence, e.g., by chemical synthesis or by the manipulation of isolated segments of nucleic acids by genetic engineering techniques.

Sequence Identity: As used herein, the term "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence of 10 nucleotides in length are identical to the corresponding positions in a second 10-nucleotide sequence, then the two sequences have 70% sequence identity. Sequence identity of a polynucleotide is typically measured using sequence analysis software (e.g., the Sequence Analysis Software Package of the Genetics Computer Group, University of Wisconsin Biotechnology Center, 1710 University Avenue, Madison, Wis. 53705).

Silent Changes: As used herein, "silent changes" refers to mutations in a nucleic acid molecule, "silent changes" are those that substitute of one or more base pairs in the nucleotide sequence, but do not change the amino acid sequence of the polypeptide encoded by the sequence.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below.

Transformed, Transfected or Transgenic: As used herein, the terms "transformed," "transfected," or "transgenic" refer to a cell, tissue, or organism into which has been introduced a foreign nucleic acid such as a recombinant vector. The terms "transformed" or "transgenic" includes progeny of a cell or organism, including progeny produced from a breeding program employing such a "transgenic" cell or organism, as a parent in a cross. For example, a transgenic $\alpha_v$-integrin or $\beta$-subunit organism is one in which an $\alpha_v$-integrin or $\beta$-subunit nucleic acid has been introduced or progeny thereof.

Polymerase chain reaction (PCR): As used herein, the term "PCR" refers to a technique to rapidly make multiple (e.g., millions to billions) copies from a segment of DNA sample. PCR uses DNA segments of interest, specific primers, heat-resistant resistant DNA polymerase enzyme, DNA nucleotides (i.e., Thymine (T), Cytosine (C), Adenine (A) and Guanine(G)). Various techniques using polymerase chain reaction (PCR) are described, e.g., in Innis et al., PCR PROTOCOLS: A GUIDE TO METHODS AND APPLICATIONS, Academic Press: San Diego, 1990. Primer pairs for PCR can be derived from known sequences by known techniques such as using computer programs intended for that purpose. Various protocols and tips exist for PCR troubleshooting and specific cases, for example, Kramer M F, Coen D M. Enzymatic amplification of DNA by PCR: standard procedures and optimization. Curr Protoc Cytom. 2006; Strien J, Sanft J, Mall G. Enhancement of PCR amplification of moderate GC-containing and highly GC-rich DNA sequences. Mol Biotechnol. 2013; 54(3):1048-1054.

Reverse transcriptase polymerase chain reaction (RT-PCR), quantitative polymerase chain reaction (qPCR), and reverse transcriptase quantitative polymerase chain reaction (RT-qPCR) methods used to identify, quantity, and amplify certain polynucleotide sequences may be performed as described in Elek et al., In vivo, 14:172-182, 2000. Methods and apparatus for chemical synthesis of nucleic acids are provided in, e.g., those provided by Applied Biosystems, Foster City, California, and Sigma-Genosys, The Woodlands, Texas.

PCR Inhibitors: As used herein, the term "PCR inhibitors" inhibit enzymes, chelate metals, and alter nucleic acids via binding or degradation. PCR inhibitors include polysaccharides, polyphenols, humic acids, melanin, hematin, hemoglobin, indigo, urea, immunoglobulin G, calcium, DNase, and RNase. These PCR inhibitors can be removed by the following techniques: precipitation; selective binding which yields a separable complex, immunocapture; heat-treated samples, dilution of the nucleic acid sample prior to PCR; and a robust DNA Polymerase. These techniques yield isolated and purified polynucleotides (DNA or RNA).

Dirty DNA/RNA: As used herein, the term "dirty DNA/RNA" refers to polynucleotides that are not isolated or purified, yet subject to PCR. Stated another way, there are two or more species of DNA segments, in dirty DNA/RNA systems. Thus, PCR acts on the two or more species of DNA segments to make multiple (e.g., millions to billions) copies of each of the two or more polynucleotides.

As used herein, threshold signal is synonymous to a minimum detectable signal. Threshold signal for a PCR reaction may be absolute (such as there is minimum absolute amount of the amplified product generated), or relative (e.g. threshold signal is generated in a mock PCR reaction run in parallel without the nucleic acid template, and the generated signal higher than the signal from the mock PCR reaction is considered to surpass a threshold signal).

It is to be understood that in the present disclosure, all embodiments are provided as illustrative and non-limiting representatives of many possible embodiments. In addition, the terms "is," "can," "will," and the like are herein used as synonyms for and interchangeable with terms such as "may," "may provide for," and "it is contemplated that the present invention may" and so forth.

Furthermore, all elements listed by name, such as a solution, HEPES buffer, probe, etc., are herein meant to include or encompass all equivalents for such elements. For example, in addition to a "HEPES buffer", any solution capable of having an equivalent effect or use is also contemplated by the present invention. Such equivalents are contemplated for each element named in its particular herein.

As used herein, M-reagent refers to a surfactant-containing amplification solution. In some embodiments, specific types of M-reagent are designated as Nona Amp A, Nona Amp B, Nona Amp C, Nona Amp D, Nona Amp E (used herein collectively as Nona Amp). S-reagent refers to an activating solution.

For purposes of summarizing, certain aspects, advantages, and novel features of the present invention are provided herein. It is to be understood that not all such aspects, advantages, or novel features may be provided in any one particular embodiment. Thus, the disclosed subject matter may be embodied or carried out in a manner that achieves or optimizes one aspect, advantage, or novel feature or group of features without achieving all aspects, advantages, or novel features as may be taught or suggested.

The compositions and method herein provide an activating solution which is mixed with a stabilized biological sample and subjected to PCR. This achieves a molecular diagnostic and detection system for pathogens amenable to PCR without having to perform a separate nucleic acid purification process.

More specifically, the compositions and methods are directed to a reagent enabling DNA and RNA analysis from biological samples with a PCR protocol. The biological sample is modified to yield a stabilized system such that: (i) the structural integrity of polynucleotides associated with a pathogen is preserved; and (ii) PCR increases the count of the polynucleotides associated with a pathogen.

Additionally, the compositions and methods herein speed up the diagnostics workflow by allowing direct (from sample) detection of DNA, RNA or other molecules present in the biological sample, by not requiring a nucleic acid extraction step.

The biological samples may include, but are not limited to, blood, urine, feces, serum, aerosol fluid, plasma, lymph, cerebrospinal fluid, saliva, mucosal secretion, vaginal fluid, ascites fluid, pleural fluid, pericardial fluid, peritoneal fluid, abdominal fluid, cell culture medium, organ culture medium, buccal cells, bacteria, viruses, yeast cells, lipids, proteins, homogenates, or extracts.

Advantages of the systems and methods herein include: (i) higher laboratory output such that at least twice the quantity of diagnostics per day are processed in comparison to the typical techniques (as described above) and (ii) the elimination of the nucleic purification process, which increases the accuracy of the molecular diagnosis and detection.

The compositions and methods herein are in contrast to currently available commercial stabilization solutions that inactivate the pathogen (e.g., an infectious agent) while preserving the nucleic acids in the stabilized biological sample. The stabilized biological sample is converted into a safe solution for biological sample transport in cases, for example, where the viral pandemic agent requires biosafety level 3 containment (e.g., SAR2-COV-2). The nucleic acids, as preserved in the stabilization solution, are traditionally purified downstream using commercially available kits or automated platforms. While purified nucleic acids are used for PCR, qPCR, and RT-qPCR techniques, sequencing, and so forth, the commercial stabilization solutions are not suitable for nucleic acid detection directly from the sample. Thus, currently commercial stabilization solutions require an expensive and time consuming nucleic acid purification step before RT-qPCR, qPCR, PCR, sequencing, and other techniques can be performed on the sample. Stated another way, the compositions and methods herein do not require the nucleic acid purification step prior to performing PCR.

The compositions and methods herein are directed to: (1) a stabilized biological sample; and (2) a set of reagents, while obviating the isolation and/or purification of polynucleotide (DNA or RNA). The stabilized biological sample and activating solution are mixed together such that polynucleotides contained within the biological sample provide a DNA segment for PCR protocols. Counts of the amplified polynucleotides, as obtained by the PCR, are used to diagnose whether the biological sample contains pathogens implicated in SARS-CoV-2 or other respiratory diseases. The counts are validated as being diagnostics by virtue of: (i) the structural integrity of the polynucleotides associated with the pathogen being maintained or not reduced; and (ii) robustness of PCR applied on these polynucleotides is increased by a contacted (or mixed) combination of the stabilized biological sample and the activating solution. The contacted or mixed combination introduce one or more of the following to the polynucleotides, as further described in the embodiments below: a surfactant/detergent, chelating agents, a pH buffer, nucleic-acid amplification enhancing agents, and reverse-transcription enhancing agents. Thus, a stabilizing effect and selectively maintaining effect for the polynucleotides are obtained for PCR treatments that increases counts of polynucleotides associated with pathogens. Without having to isolate these polynucleotides, the contacted (or mixed) combination of the stabilized biological sample and the activating solution increases an effective concentration of the polynucleotides associated with pathogens in the combination. The increase in the effective concentration of the polynucleotides associated with pathogens leads to systems enriched with polynucleotides associated with pathogens. In this enriched state, the polynucleotides associated with pathogens are more amenable to PCR over other polynucleotide species. Thus, the diagnostic value of the compositions and methods herein is increased.

In some embodiments, the compositions herein may further comprise nucleic-acid amplification enhancing agents known to act as an adjuvant in molecular diagnostics. Nucleic-acid amplification enhancing agents include but are not limited to: bovine serum albumin (BSA), dimethyl sulfoxide (DMSO), glycine, trehalose, polyethylene glycol (PEG), trimethylglycine (betaine), deoxynucleotide triphosphate, tetramethylene (TM) sulfone, TM sulfoxide, formamide, glycerol, tetramethylammonium (TMA) chloride, TMA oxalate, ammonium sulfate, acetamide, and 2-pyrrolidone.

In some embodiments, the composition herein may further comprise reverse-transcription enhancing agents to enhance the performance of the reverse transcriptase enzyme. The reverse-transcription enhancing agents include but are not limited to trehalose, glycerol, and formamide.

In some embodiments, the compositions herein comprise chelating agents that can bind to monovalent, divalent, and polyvalent cations. The chelating agents used herein include but are not limited to ethylene glycol tetraacetic acid (EGTA); trans-1,2-diaminocyclohexane-N,N,N',N'-tetraacetic acid (CDTA); diethylenetriaminepentaacetic acid (DTPA); ethylenediaminetetraacetic acid (EDTA); 1,4,7,10-tetraazacyclododecane-1,4,7,10-tetraacetic acid (DOTA); 1,2-bis(2-aminophenoxy)ethane-N,N,N',N'-tetraacetic acid (BAPTA); N-(2 hydroxyethyl)ethylenediamine-N,N',N'-triacetic acid; nitrilotriacetic acid (NTA). The chelating agents antagonistically bind to ribonucleoside vanadyl complexes (RVC) and/or other hexacoordinate ions. The chelating agent can be added or found in combination with a pH stabilizing buffer solution.

In some embodiments, the compositions herein comprise: a pH stabilizing buffer solution. The pH stabilizing buffer solution includes but is not limited to IVIES (2-(N-morpholino)ethanesulfonic acid); MOPS (3-(N-morpholino)propanesulfonic acid); MOPSO (3-morpholino-2-hydroxypropanesulfonic acid); HEPES (4(2 hydroxyethyl)piperazine-1-ethanesulfonic acid; Tri(tris(hydroxymethyl)aminomethane); Bis-Tris (2-[Bis(2-hydroxyethyl)amino]2(hydroxymethyl)-1,3-propanediol); sodium or potassium phosphate buffer, PBS (Phosphate-buffered saline); HBSS (Hank's Balanced Salt Solution); and acetate buffer In some embodiments, a PCR mastermix is supplemented with mastermix additives. The mastermix additives comprise surfactant reagents and PCR enhancing reagents.

In some embodiments, a mastermix additive (M-reagent) is a surfactant-based solution containing PCR enhancing agents In some embodiments, a sample diluent (S-reagent) is a buffer-based solution. In one embodiment, S-reagent has the following composition: Tris 10 mM pH 7.4.

In some embodiments, nucleic acids are made available for amplification by sample diluent reagent (S-reagent).

In some embodiments, one or more elements disclosed herein may be used separately or in conjunction with other elements. For example, the quenching agent(s) may be added to a commercially available nucleic acid stabilizing reagent that is not present as part of the kit of the present invention.

In some embodiments, a kit is provided for sampling, genome stabilization, pathogen inactivation, and room temperature transport of SARS-CoV-2 and other respiratory viruses. The kit includes a swab for transferring a sample to a plurality of tubes. Each tube of the plurality of tubes contains transport solution for containing a biological sample. The biological sample in the transport solution is mixed with the S-reagent. Stated another way, the S-reagent supplements the biological sample. A buffered surfactant solution, i.e., M-reagent, is added to a mastermix to make the activating solution. Stated another way, the M-reagent supplements the mastermix. The mastermix may be for RT-qPCR, qPCR, PCR, and other techniques. In each tube, a biological sample is mixed with the activating solution. Thus, the biological sample, which is supplemented with S-reagent, is contacted with M-reagent supplemented mastermix. A well for housing each tube is sent to a thermocycler.

In some embodiments, transport solution for stabilizing nucleic acids comprises a chaotropic agent and a chelating agent, and the transport solution stabilizes a nucleic acid molecule of the pathogen at room temperature for at least 2 days. The chaotropic agent in the transport solution is selected from the following group: guanidine hydrochloride, guanidine thiocyanate, potassium thiocyanate, sodium thiocyanate, urea, and the chelating agent in the transport solution is selected from the following group: diethylenetriaminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, nitrilotriacetic acid (NTA). In some preferred embodiments, the chaotropic agent in the transport solution is guanidine thiocyanate at a concentration of 0.5M, 1M, 2M, 3M, 4M, 5M or 6M, and the chelating agent is EDTA at a concentration of 20 mM, 30 mM, 40 mM, 50 mM or 60 mM. In some embodiments, transport solution does not contain a buffer. In some embodiments, transport solution further comprising a buffer having pH from 7.0 to 9.5, a reducing agent and a detergent, wherein the reducing agent is selected from the following group: 2-mercaptoethanol, thiosulfate, tris-(2-carboxyethyl) phosphine (TCEP), dithiothreitol, dithioerythritol, and the detergent is selected from the following group: Triton X-100, Tween 20, Tween 80, Nonidet P-40, Brij 35, an ethoxylated amine detergent, an alkylbenzene sulfonate detergent, sodium dodecyl sulfate (SDS). In some embodiments, the transport solution comprises a Tris-HCL buffer having pH from 7.0, 7.5, 8.5, 9.0 or 9.5 at a concentration of 50 mM, 75 mM, 100 mM, 125 mM, or 150 mM.

In some embodiments, the amplification solution (M-reagent) comprises a non-ionic surfactant at a concentration of 0.5 to 5 percent (vol./vol.), and optionally comprises at least one nucleic-acid amplification enhancing agent. In some embodiments, S-reagent is first added to a sample in the transport solution, and then M-reagent is added along with a PCR Mastermix containing a primer set, polymerase enzyme and corresponding polymerase enzyme buffer. In some embodiments, nucleic-acid amplification enhancing agent used in M-reagent is BSA at a concentration of 0.3%, 0.5%, 0.8%, 1%, 2% or 3% (vol./vol.). In some embodiments, nucleic-acid amplification enhancing agent used in M-reagent is DMSO at a concentration of 0.5%, 1%, 2%, 3%, 3.5%, 4%, 4.5% or 5% (vol./vol.). In some embodiments, nucleic-acid amplification enhancing agent used in M-reagent is glycerol at a concentration of 0.5%, 0.8%, 1%, 2%, 3% or 5% (vol./vol.).

Preliminary studies of the compositions and methods herein demonstrate that dilution of a biological sample stabilized in a commercial reagent allows for direct amplification when diluted in Buffer. Several experiments are conducted to test whether the reagent, method, and kit of the present invention allow for direct amplification without altering the limit of detection observed with an industry-standard nucleic acid purification step before detection using techniques generally disclosed herein.

Examples

Aspects of the present teachings may be further understood in light of the following examples, which should not be construed as limiting the scope of the present teachings in any way.

The premise for this research is that samples stabilized in commercial stabilization reagents contain unidentified RT-qPCR inhibitors (i.e., PCR inhibitors as described above) that upon dilution interfere with the amplification step. Possible inhibitors of RT-qPCR reactions are chelating agents such as EDTA, SDS or other detergents, and others.

The experimental results, disclosed generally herein, are conducted to test potential quenchers of the inhibitors present in the stabilizing reagent, and potentially in other commercial stabilizers, so that nucleic acids are detected at a lower dilution factor.

As used in these examples, exemplary Nona Amp solutions represent variations of the surfactant-containing amplification solution (or M-reagent). Specifically, Nona Amp formulation A is Tween® 20 1%; B=Tween® 20 1%+DMSO 5%; C=Tween® 20 2%+NP40 2%; D=Tween® 20 2%+NP40 2%+DMSO 5%; E=Tween® 20 10%. The exemplary composition of activating solution (S-reagent) is as follows: Buffer Tris 10 mM pH 7.4. Other tested S-reagents include HEPES, phosphate, MOPS, MES, Borate buffers having pH from 6.8 to 8.2 at a concentration of 5 mM to 20 mM. Preferably, the stabilized sample is diluted with the activating solution by a factor of 50 or by a factor of 100, or by a factor of 200.

Different compositions of the transport solution have been tested for sample stabilization and subsequent nucleic acid amplification using S-reagent and M-reagent. In some embodiments, the composition of the transport solution are as follows: 50 mM Tris-HCL pH 9 20 mM EDTA+2M GuSCN; 100 mM Tris-HCL pH 8.5+40 mM EDTA+4M GuSCN; 40 mM EGTA+4M KSCN; or DNA/RNA Shield™ from Zymo Research. In the experiments described below or similar to them, all above mentioned transport solutions show non-inferior results as compared to DNA/RNA Shield™ from Zymo Research, which is considered a gold standard transport solution. In all embodiments, transport solutions stabilize a nucleic acid molecule at room temperature for at least 48 hours.

Experiment 1: Validation of Nona Amp Reagent a with a Commercially Available SARS-CoV-2 Detection Kit and Two Different RT-qPCR Commercial Amplification Kits Experiment 1 evaluates whether a primary reagent, Nona Amp A, allows RT-qPCR detection of the RNAse P messenger RNA from a direct human tissue sample preserved in a nucleic acid transport solution without the RNA extraction step. Nona Amp A is validated as having increased detection capability with RNaseP using the two mastermixes (MM1 and MM2) at two different sample dilutions.

A commercially available SARS-CoV-2 detection kit is used in combination with two different RT-qPCR commercial amplification kits that are widely used for such detection assays (master mix 1 and master mix 2).

Two different final sample dilutions—D1 and D2—are used. D1 is the less diluted solution, and D2 is the more diluted solution. D1 has a dilution factor of 1:50 and D2 has a dilution factor of 1:100.

RT-qPCR is performed with and without Nona Amp A of the activation solution herein according to the following protocol.

Activation Solution: RT-qPCR mix preparation with Nona Amp A:

(1) The RT-qPCR mastermix is prepared via the protocol indicated by the commercial kit except for supplementing with Nona Amp A 10× to reach 1×. The mix for each reaction is added to the adequate PCR tubes.

More specifically, Nona Amp A is provided at a concentration 10× and reduced to concentration of 1×. Different RT-qPCR mastermixes or detection kits recommend different final volumes. For example, the CDC detection kit recommends using a final volume of 20 µL while the Thermofisher detection kit recommends using a final volume of 25 µL.

(2) Sample preparation: Nasopharyngeal samples are taken using a certified swab; placed onto a 2-mL tube containing 1000 µL of transport media; and mixed. After at least 1 hour of inoculation, a certain amount of sample is mixed with the sample diluent component of Nona Amp A.

(3) A 5-µL of sample mix is added to the RT-qPCR mix, and detection is done according to the manufacturer's recommendations.

Mastermix 1 (MM1) is Brilliant III Ultra-Fast QRT-PCR Master Mix #60884, as provided by Agilent.

Mastermix 2 (MM1) is one-step RT-qPCR Master Mix TaqMan™ Fast Virus 1-Step (#4444436), as provided by Thermo Fisher.

Results show that Nona Amp formulation A allows RNAseP detection from a direct sample stabilized with this specific transport media with both RT-qPCR mastermixes used. With the less diluted sample (D1), amplification is not obtained in the absence of Nona Amp A (FIG. 1). In comparison, addition of Nona Amp A to the reaction gives positive results when used with MM1 mastermix (FIG. 1), indicating that Nona Amp A of the activation solution effectively counteracts the inhibitors present in the transport media at low dilutions of the sample.

The activation solution containing MM2 RT-qPCR Master Mix is less efficient at amplifying the desired RNA at this concentration, as no amplification is observed with Nona Amp A (FIG. 1).

When tested with a more diluted sample, Nona Amp A supplementation in the activation solution allows RT-qPCR detection from the direct sample with both one-step RT-qPCR mastermixes (FIG. 1). In the absence of Nona Amp A, amplification is not observed.

TABLE 1

COUNT OBTAINED FROM EXPERIMENT 1

|  | No additive | With Nona AmpA |
| --- | --- | --- |
| MM1 - D1 | No Count | 30.54 |
| MM1 - D2 | 30.82 | 31.16 |
| MM2 - D1 | No Count | No Count |
| MM2 - D2 | No Count | 39.55 |

In summary, these results show that Nona Amp A in the activation solution blocks the inhibitory effect of the transport media, allowing detection of RNaseP via RT-qPCR from a direct sample without RNA extraction.

Experiment 2: Determination of Efficacy of Different Nona Amp Compositions Contained within the Activation Solutions To strengthen the power of Nona Amp in neutralizing the inhibitory effect of different transport/stabilizing solution, different compositions of Nona Amp (A-E) are evaluated as to their respective effect on RNAseP amplification from stabilized samples using the first SARS-CoV-2 detection kit used with MM1 mastermix as shown in Experiment 1. Results are shown in TABLE 2.

Nona Amp A, Nona Amp B, Nona Amp C, Nona Amp D, and Nona Amp E are buffered solutions which contain at least one surfactant and/or one enhancing agent.

In Experiment 2, Nona Amp D and Nona Amp E is observed to improve RT-qPCR detection of RNaseP from stabilized samples, as Nona Amp D and Nona Amp E allow for detection at a lower sample dilution. Nona Amp A-C does not improve or impair RNAseP amplification.

These results indicate that different formulations of Nona Amp in the activation solutions can specifically improve RT-qPCR detection from direct samples using different detection kits, several RT-qPCR mastermixes and various sample stabilizing solutions.

TABLE 2

COUNTS OBTAINED FROM EXPERIMENT 2

|  | D1 | D2 |
| --- | --- | --- |
| Nona Amp-A | No Count | 31.4 |
| Nona Amp-B | No Count | 32.48 |
| Nona Amp-C | No Count | 32.58 |
| Nona Amp-D | 32.27 | 34.08 |
| Nona Amp-E | 37.71 | 34.35 |
| Without Nona Amp | No Count | 32.7 |

Experiment 3: Validation of Buffer Nona Amp with Multiple SARS-CoV-2 Samples Using a SARS-CoV-2 Detection Kit A Experiment 3 further validates the efficacy of a specific Nona Amp in the activation solution to allow for RT-qPCR detection from samples without nucleic acid extraction. More specifically, Nona Amp is tested with several stabilized samples utilizing a SARS-CoV-2 assay kit A SARS-CoV-2 assay kit A is Quick-SARS-CoV-rRT-PCR kit from Zymo Research (#R3011)

Figure 2A:
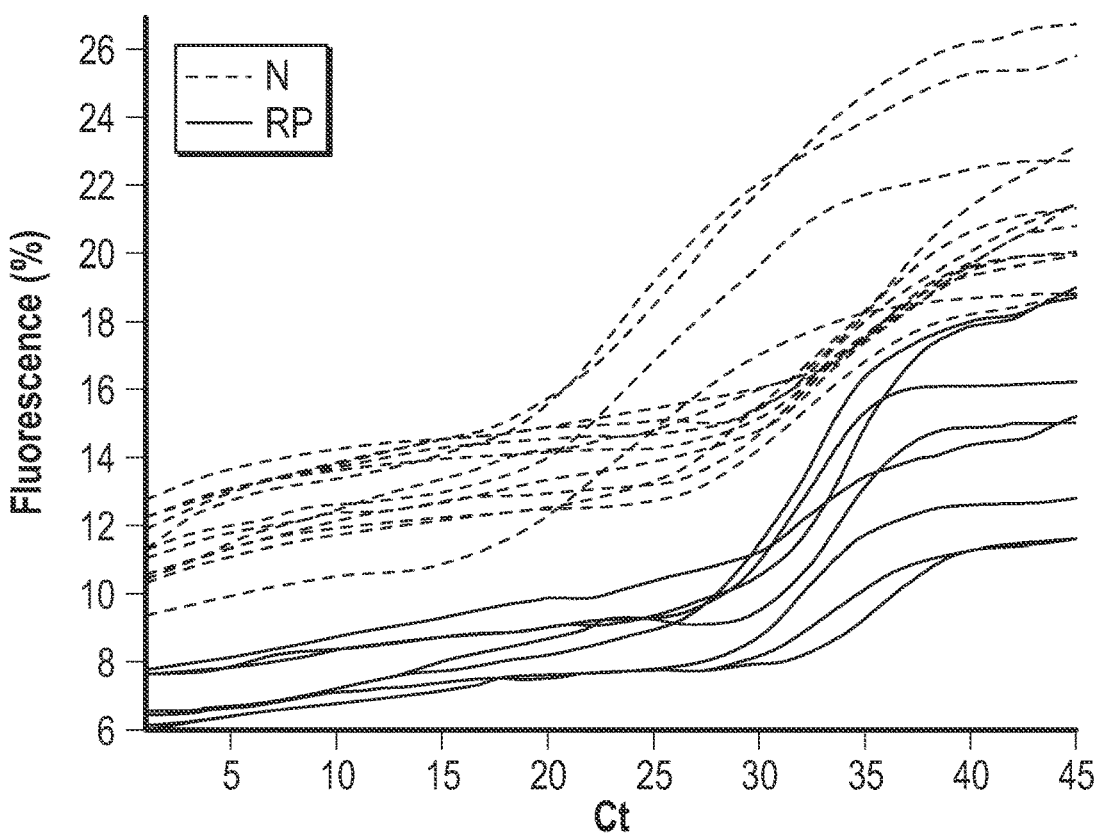
FIG. 2A-FIG. 2D. Nona Amp® allows SARS-CoV-2 detection directly from nasopharyngeal swab samples using Zymo's diagnostic platform. Nasopharyngeal swab samples (N=80) preserved in DNA/RNA Shield™ transport solution (Zymo Research) were subjected to RT-qPCR to detect SARS-CoV-2 N messenger RNAs using an alternative version of the Quick SARS-CoV-2 rRT-PCR Kit (#R3011, Zymo Research).

For comparison, SARS-CoV-2 detection of the same samples are assessed but with the RNA extraction step. Results are shown in FIG. 2A.

In Experiment 3, Nona Amp is observed to successfully allow for RT-qPCR amplification from direct stabilized samples without RNA extraction across different samples.

Figure 2B:
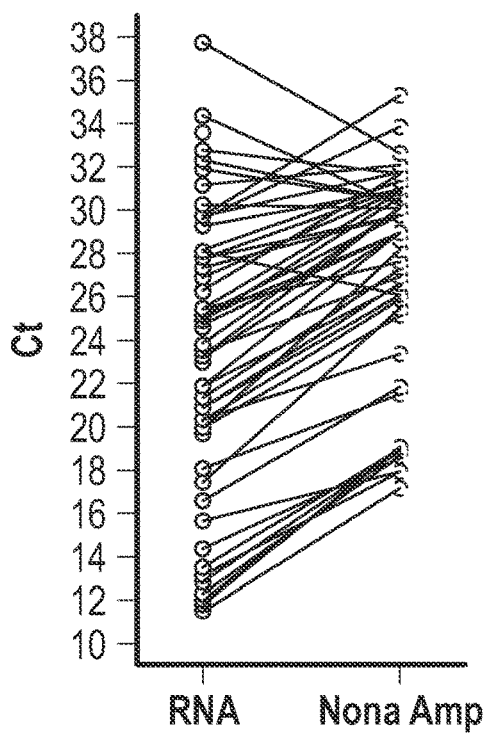
Figure 2C:
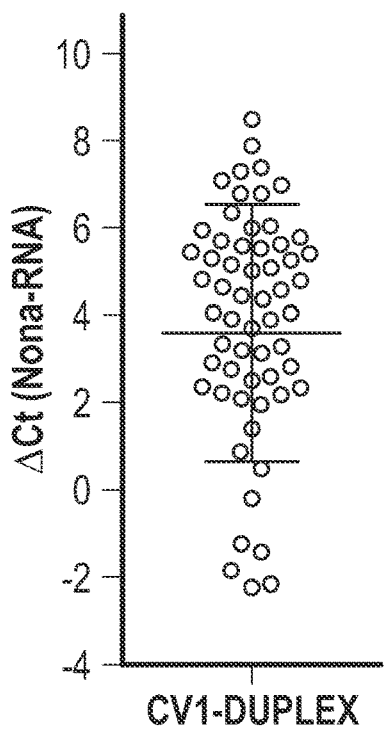

In Experiment 3, the Ct correlation with this specific Nona Amp is around 4 count higher than the same sample when analyzed using purified RNA (FIG. 2B and FIG. 2C).

Figure 2D:
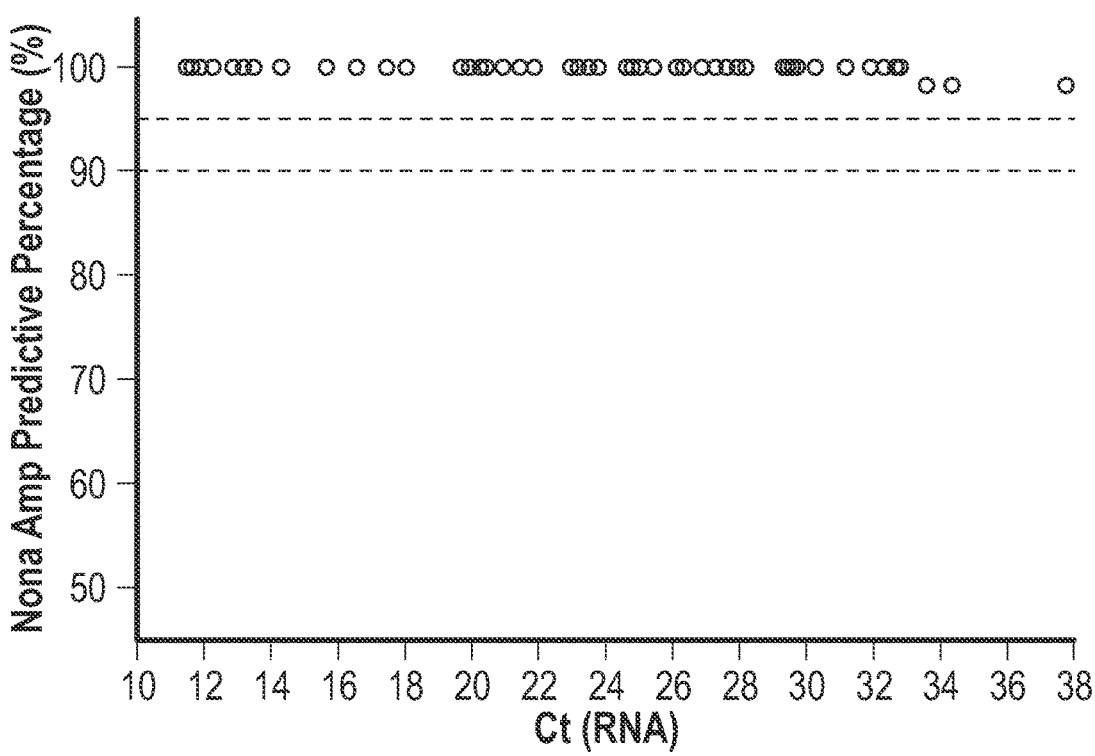

In Experiment 3, Nona Amp is observed to have a 100% of SARS-CoV-2 detection correlation when compared with purified RNA (FIG. 2D).

Experiment 3 is performed with 80 nasopharyngeal samples and stabilized with DNA and RNA transport and storage medium (e.g., DNA/RNA Shield™) stabilizing solution.

Experiment 4: Validation of Buffer Nona Amp with Multiple SARS-CoV-2 Samples Using a SARS-CoV-2 Detection Kit B Experiment 4 further validates the efficacy of a specific Nona Amp in the activation solution to allow for RT-qPCR detection from samples without nucleic acid extraction. More specifically, Nona Amp is tested with several stabilized samples utilizing a SARS-CoV-2 assay kit B.

SARS-CoV-2 assay kit B is TaqMan 2019-nCoV assay Kit v1 Detection Kit (#A47532, Thermofisher) with the TaqPath 1-Step RT-qPCR Master Mix, CG (#A47532, Thermofisher).

SARS-CoV-2 assay kit B assesses amplification of three different viral messenger RNAs; ORF, S and N.

Figure 3A:
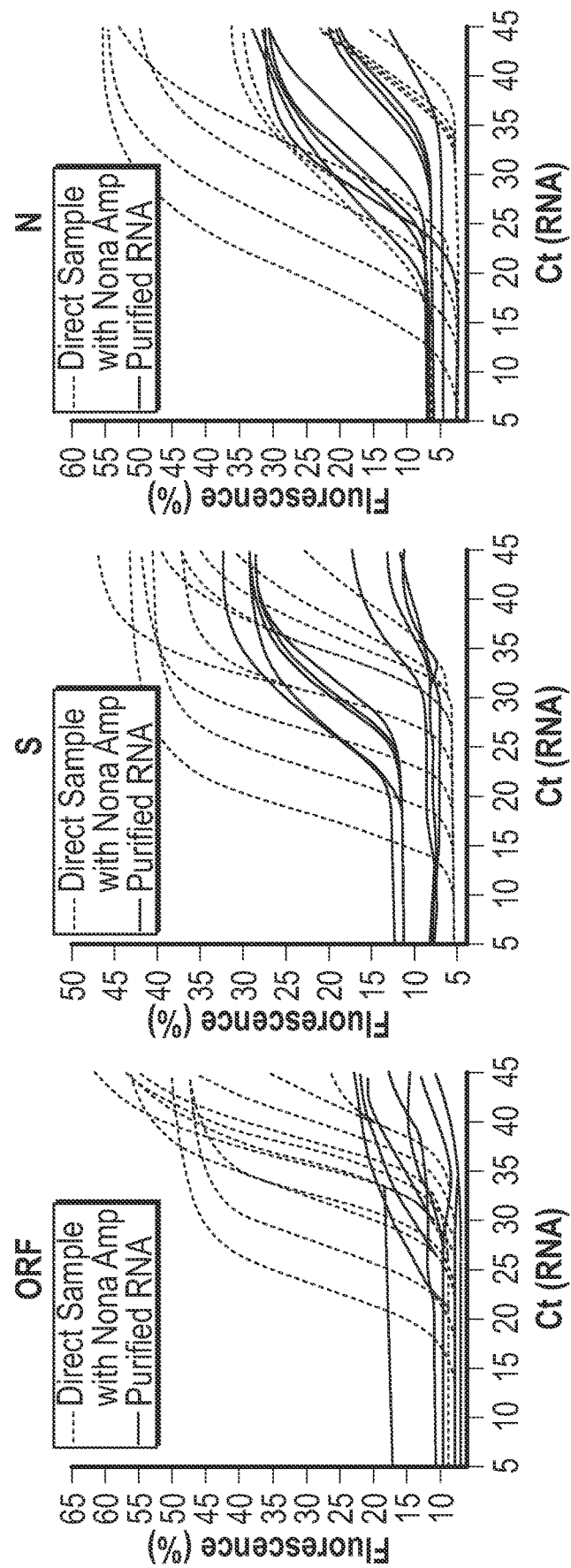
FIG. 3A-FIG. 3D. Nona Amp® allows SARS-CoV-2 detection directly from nasopharyngeal swab samples using Thermofisher's diagnostic platform. Nasopharyngeal swab samples preserved in DNA/RNA Shield™ (Zymo Research) transport solution (N=60) were subjected to RT-qPCR to detect SARS-CoV-2 S, N and ORF messenger RNAs using the TaqMan 2019-nCoV Assay Kit v1 detection kit (#A47532) with the TaqPath 1-Step RT-qPCR Master Mix, CG (#A15300).

For comparison, SARS-CoV-2 detection of the same samples are assessed but with the RNA extraction step. Results are shown in FIG. 3A.

In Experiment 4, Nona Amp successfully allows RT-qPCR amplification from direct stabilized samples without RNA extraction across different samples for the three assessed target RNAs.

Figure 3B:
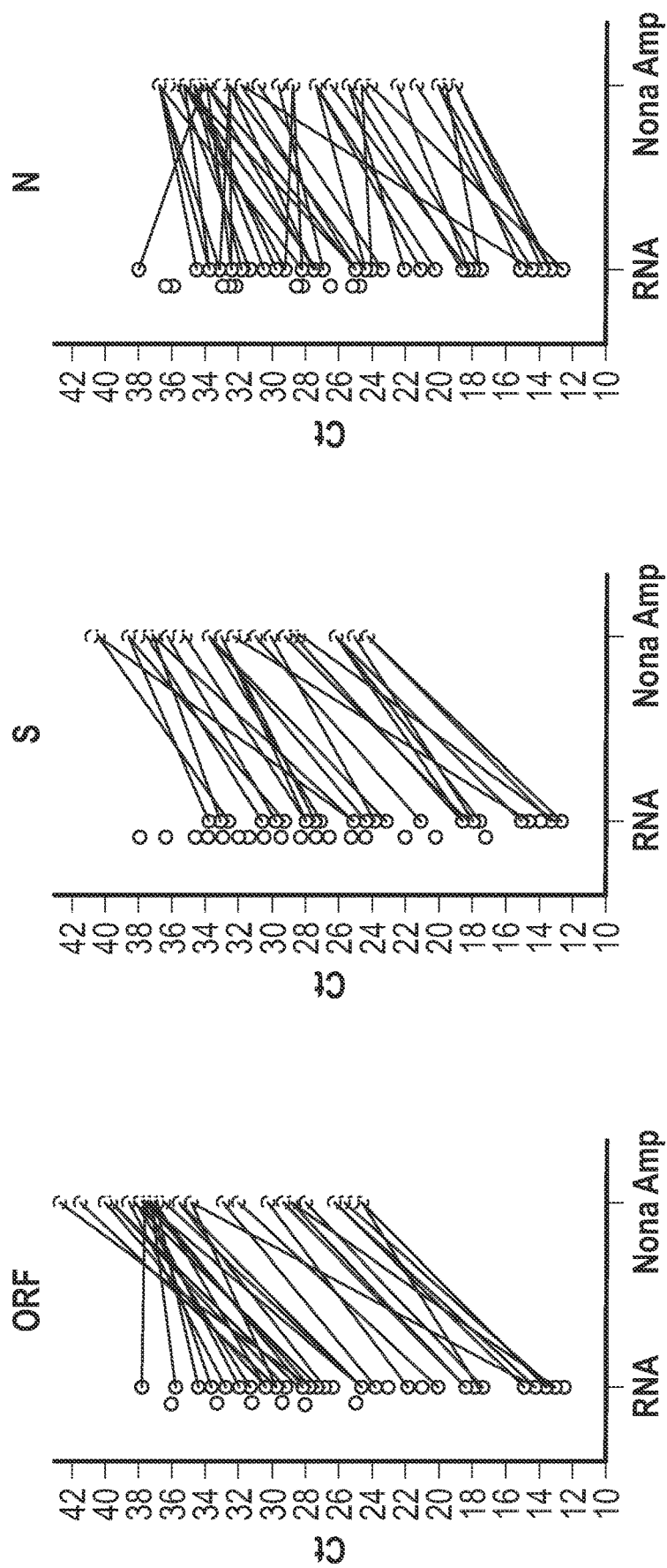
Figure 3C:
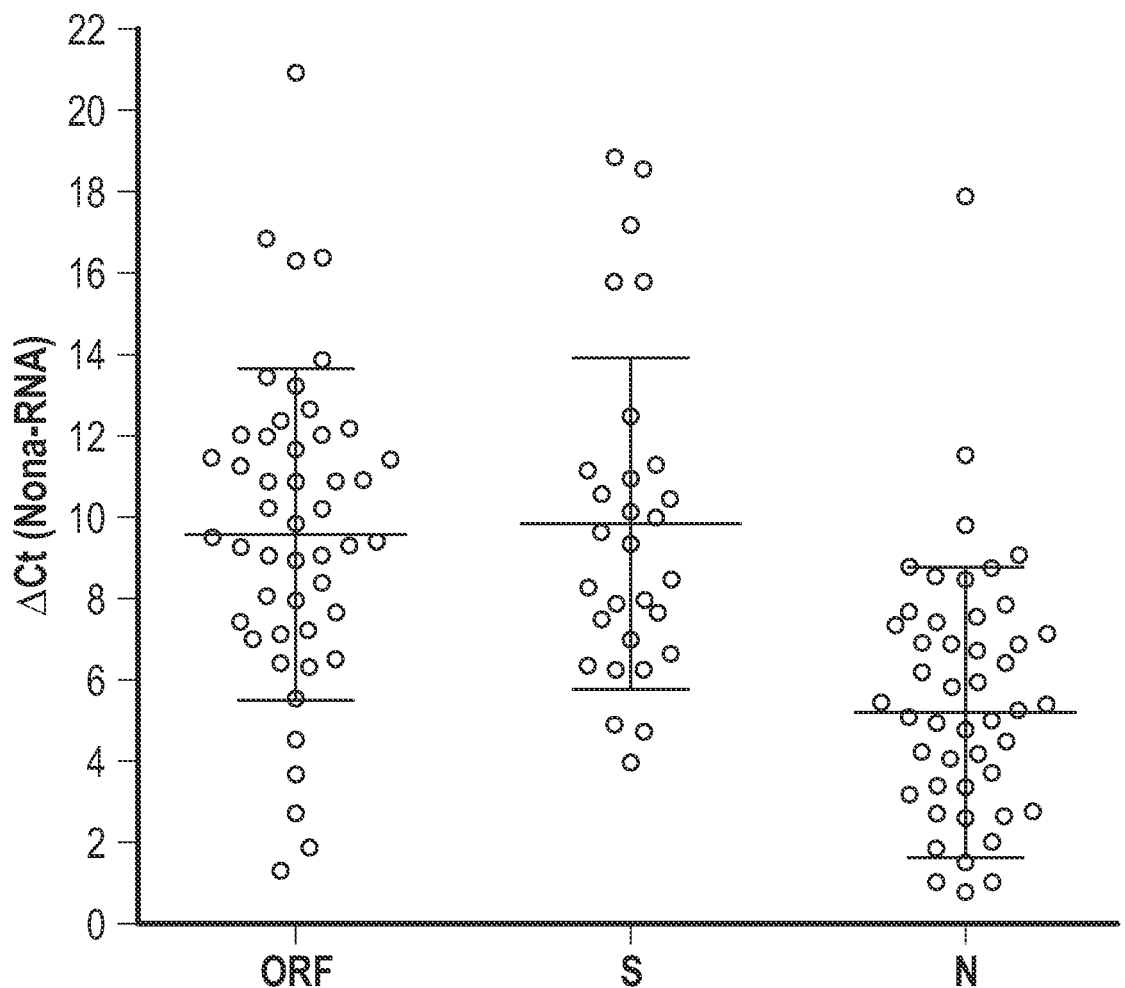

The Ct correlation with this specific Nona Amp is around 9 count higher than the same sample when analyzed using purified RNA for ORF, 10 for S and 5 for N (FIG. 3B and FIG. 3C).

Figure 3D:
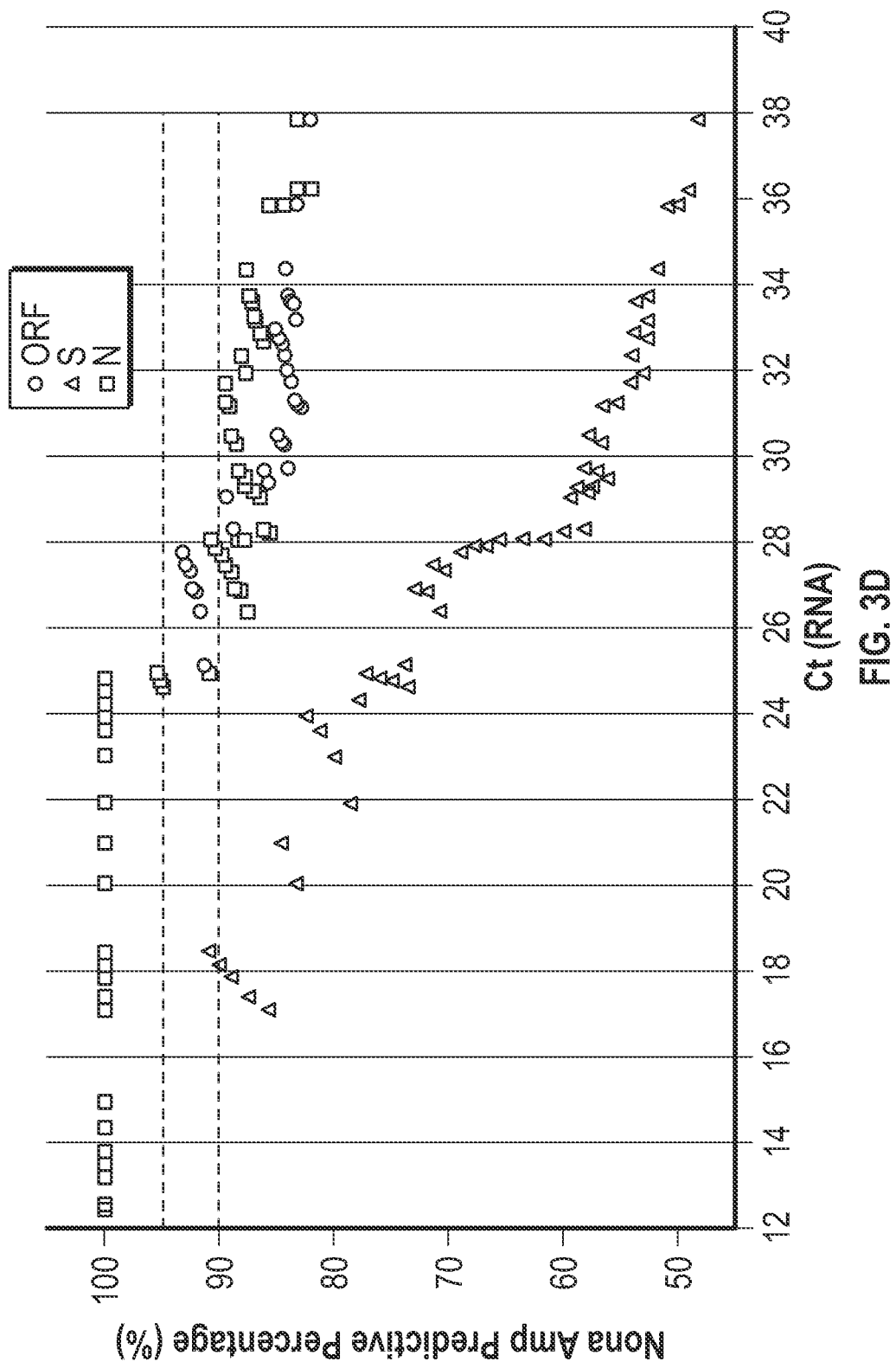

In Experiment 4, Nona Amp is observed to have a 90% of correlation for SARS-CoV-2 detection with samples that have a Ct<30 with purified RNA(FIG. 3D).

Experiment 4 is performed with 60 nasopharyngeal samples and stabilized with DNA and RNA transport and storage medium (e.g., DNA/RNA Shield™) stabilizing solution.

Experiment 5: Validation of Buffer Nona Amp with Multiple SARS-CoV-2 Samples Using a SARS-CoV-2 Detection Kit C Experiment 5 further validates the efficacy of a specific Nona Amp in the activation solution to allow for RT-qPCR detection from samples without nucleic acid extraction. More specifically, Nona Amp is tested with several stabilized samples utilizing a SARS-CoV-2 assay kit C SARS-CoV-2 assay kit C is SARS-CoV-2 RdRp messenger RNA using the LightMix® Modular Wuhan CoV RdRP-gene kit (#53-0777-96, Roche).

Figure 4A:
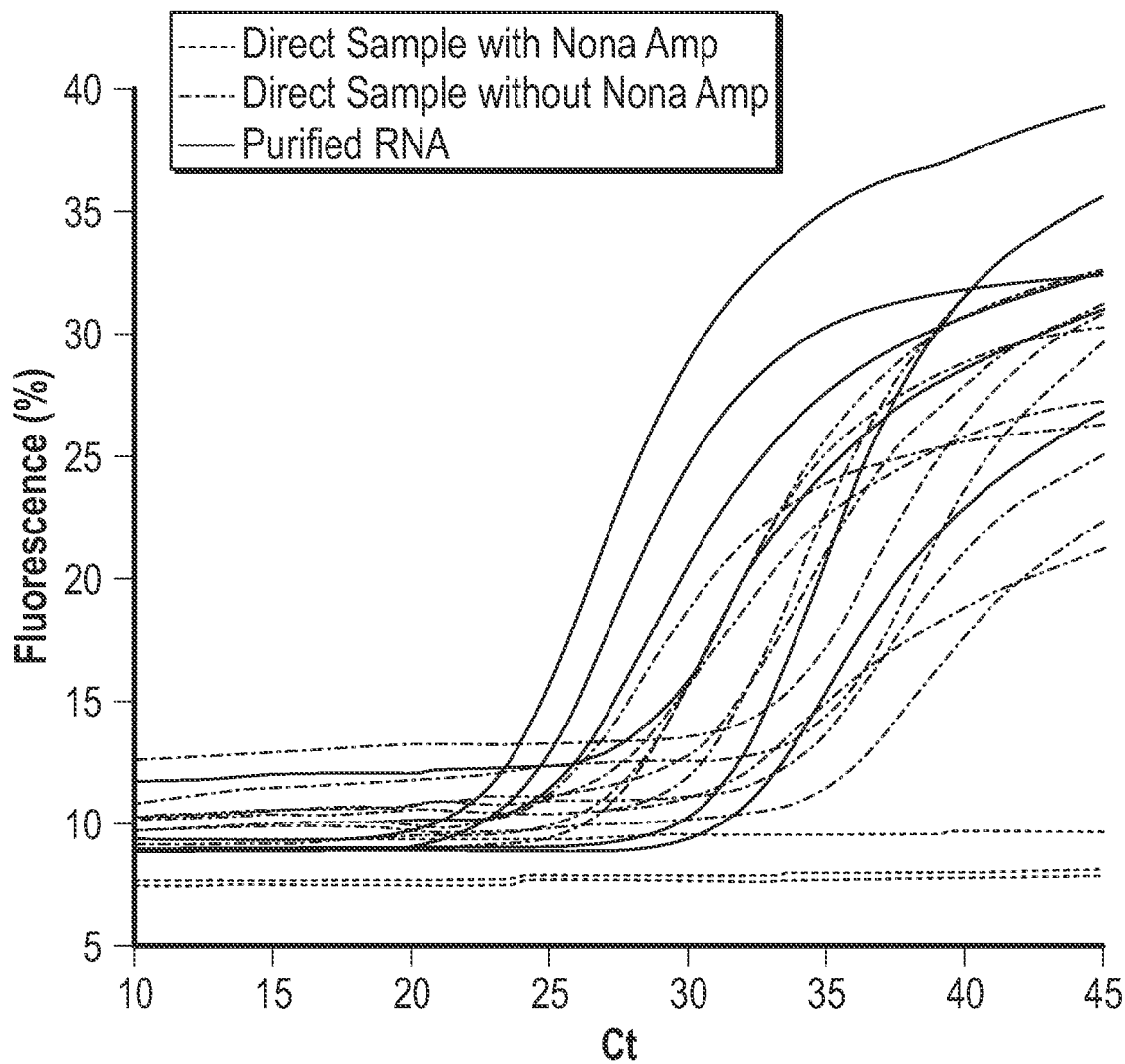

For comparison, SARS-CoV-2 detection of the same samples are assessed but with the RNA extraction step. Results are shown in FIG. 4A.

In Experiment 5, Nona Amp is observed to successfully allow for RT-qPCR amplification from direct stabilized samples without RNA extraction across different samples.

Figure 4C:
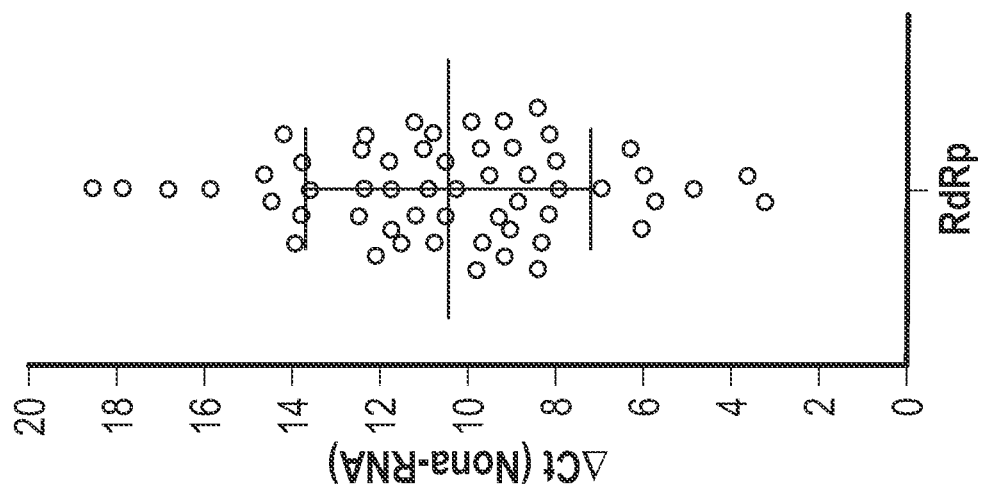
Figure 4B:
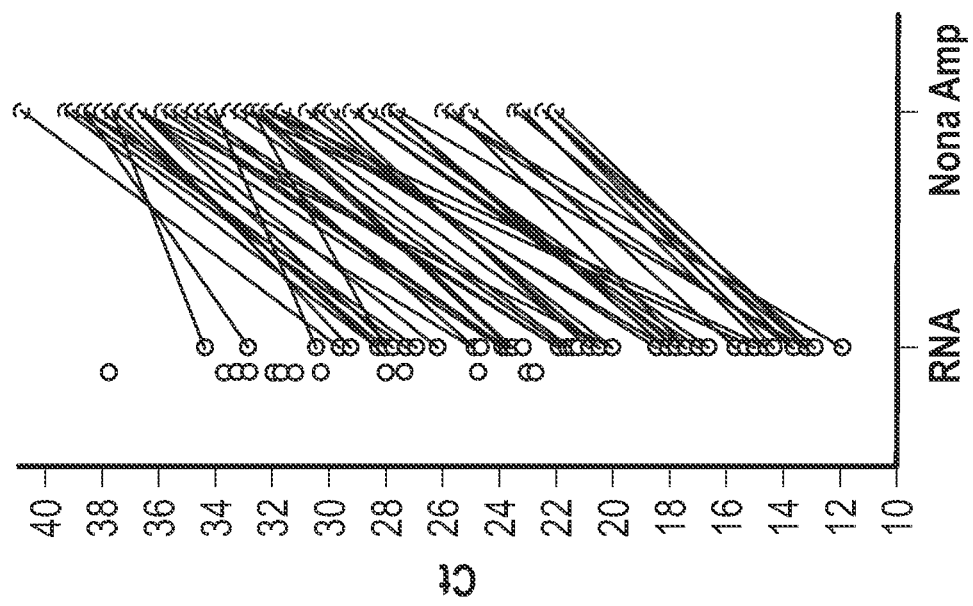

In Experiment 5, the Ct correlation with this specific Nona Amp is around 10 count higher than the same sample when analyzed using purified RNA (FIG. 4B and FIG. 4C).

In Experiment 5, Nona Amp is observed to have a 90% of SARS-CoV-2 detection correlation with samples that have a Ct<30 with purified RNA (FIG. 4D).

Experiment 5 is performed with 80 nasopharyngeal samples and stabilized with DNA and RNA transport and storage medium (e.g., DNA/RNA Shield™) stabilizing solution.

Experiment 6: Validation of Buffer Nona Amp with Multiple Samples Stabilized with a Different Transport Solution Using SARS-CoV-2 Detection Kit A Experiment 6 is performed with 6 nasopharyngeal samples stabilized with DNA and RNA transport solution. Several variants of transport solutions were tested, each producing a comparable result after amplification, for example, solution 1: 100 mM Tris-HCL pH 8.5+40 mM EDTA+4M GuSCN; solution 2: 50 mM Tris-HCL pH 8+20 mM EDTA+4M KSCN; solution 3: 150 mM Tris-HCL pH 8+40 mM EGTA+2M NaSCN.

The efficacy of a Nona Amp in the activation solution was validated to allow for RT-qPCR detection from samples without nucleic acid extraction. More specifically, Nona Amp is tested with several SARS-CoV-2 negative samples stabilized in the transport solution utilizing a SARS-CoV-2 assay kit C.

Figure 5A:
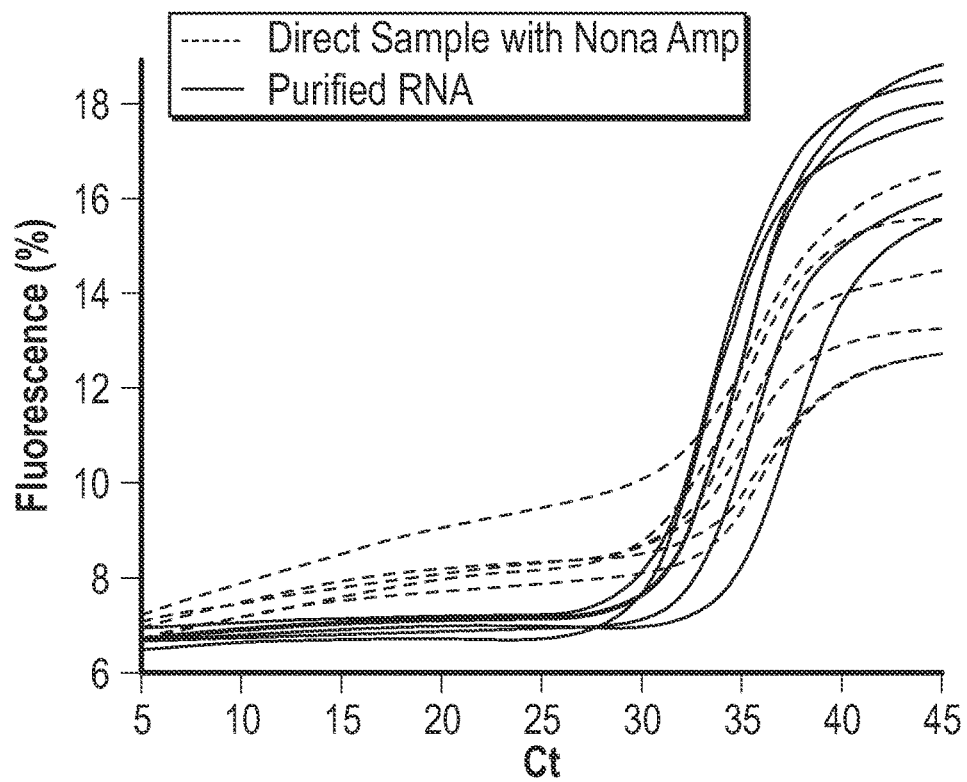
FIG. 5A-FIG. 5B. Nona Amp® allows RNAseP detection directly from nasopharyngeal swab samples preserved in a nucleic acid transport solution. Nasopharyngeal swab samples (N=6) preserved in the transport solution (100 mM Tris-HCL pH 8.5+40 mM EDTA+4M GuSCN) were subjected to RT-qPCR to detect RNAseP messenger RNAs using Zymo's diagnostic platform (an alternative version of Quick SARS-CoV-2 rRT-PCR Kit, Zymo Research).

For comparison, RNAseP detection of the same samples are assessed but with the RNA extraction step. Results are shown in FIG. 5A.

In Experiment 6, Nona Amp is observed to successfully allow for RT-qPCR amplification from direct stabilized samples without RNA extraction across different samples.

Figure 5B:
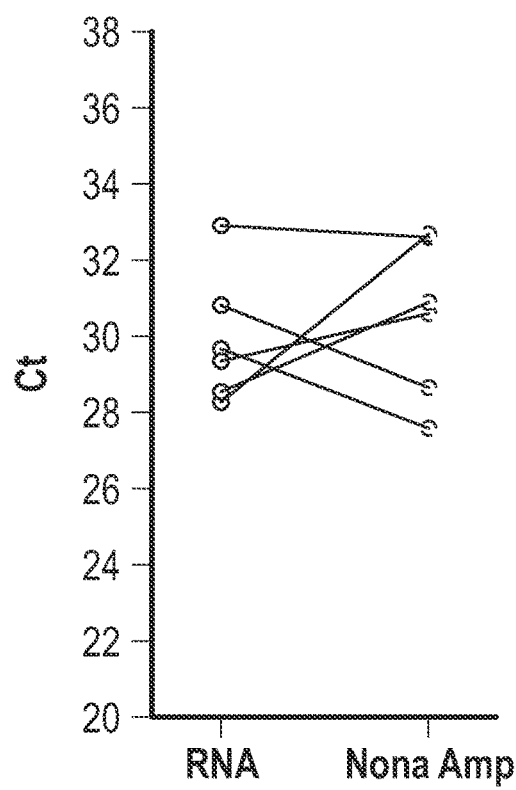

In Experiment 6, the Ct correlation with this specific Nona Amp is similar to the same sample when analyzed using purified RNA (FIG. 5B).

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for detecting genetic material, the method comprising:
    (a) obtaining a stabilized biological sample, the stabilized biological sample comprising a biological sample and a transport solution, wherein the transport solution comprises a chaotropic agent and a chelating agent, and wherein the transport solution stabilizes nucleic acid molecules in the stabilized biological sample at room temperature, wherein the nucleic acid molecules comprise genetic material from a pathogen, a host, or a combination of the pathogen and the host;
    (b) without prior extraction of the nucleic acid molecule present in the stabilized biological sample, mixing the stabilized biological sample with an activating solution to form a stabilized and activated biological sample, the activating solution comprising a buffer having pH from 6.8 to 8.2;
    (c) combining the stabilized and activated biological sample to an amplification reaction mixture, wherein the amplification reaction mixture antagonizes the effect of inhibitors of enzymatic reactions, wherein the enzymatic reaction comprises DNA polymerization and reverse transcription of RNA, wherein the amplification reaction mixture comprises an amplification solution, DNA polymerase enzymes, a DNA polymerase buffer, and primer sets and probes specific for the nucleic acid molecules, wherein the amplification solution comprises a non-ionic surfactant at a concentration of 0.5 to 5 percent (vol./vol.);
    (d) subjecting the amplification reaction mixture to a polymerase chain reaction (PCR), wherein the PCR amplifies the nucleic acid molecule;
    (e) detecting the pathogen in the stabilized biological sample when a signal generated in the polymerase chain reaction surpasses a threshold signal for the polymerase chain reaction.

2. The method of claim 1, wherein the nucleic acid molecule is a ribonucleic acid (RNA) and a corresponding DNA molecule is produced from the RNA by a reverse transcriptase enzyme prior to or simultaneously with the polymerase chain reaction.

3. The method of claim 2, wherein the polymerase chain reaction is an RT-PCR, RT-qPCR or one-step RT-qPCR.

4. The method of claim 1, wherein the non-ionic surfactant in the amplification solution is at a concentration of 0.5 to 10 percent (vol./vol.) and is selected from the group consisting of 2-[2-[4-(2,4,4-trimethylpentan-2-yl)phenoxy]ethoxy]ethanol, Octylphenoxypolyethoxyethanol Polyoxyethylene (20) sorbitan monolaurate, Polyoxyethylene (80) sorbitan monooleate, and 2-[4-(2,4,4-trimethylpentan-2-yl)phenoxy]ethanol).

5. The method of claim 4, wherein the amplification solution further contains at least one nucleic-acid amplification enhancing agent.

6. The method of claim 5, wherein the at least one nucleic-acid amplification enhancing agent is selected from the group consisting of bovine serum albumin (BSA), dimethyl sulfoxide (DMSO), glycine, trehalose, polyethylene glycol (PEG), trimethylglycine (betaine), dNTPs, tetramethylene (TM) sulfone, TM sulfoxide, formamide, glycerol, tetramethylammonium (TMA) chloride, TMA oxalate, ammonium sulfate, acetamide, and 2-pyrrolidone.

7. The method of claim 6, wherein the nucleic-acid amplification enhancing agent is selected from the group consisting of BSA at a concentration of 0.3 to 3 percent (vol./vol.), DMSO at a concentration of 0.5 to 5 percent (vol./vol.), and glycerol at a concentration of 0.5 to 5 percent (vol./vol.).

8. The method of claim 1, wherein the chaotropic agent in the transport solution is selected from the group consisting of guanidine hydrochloride, guanidine thiocyanate, potassium thiocyanate, sodium thiocyanate, urea, and the chelating agent in the transport solution is selected from the group consisting of diethylenetriaminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, and nitrilotriacetic acid (NTA).

9. The method of claim 8, wherein the chaotropic agent in the transport solution is guanidine thiocyanate at a concentration of 0.5M to 6M, and the chelating agent is EDTA at a concentration of 20 mM to 60 mM.

10. The method of claim 8, wherein the transport solution further comprising a buffer having pH from 7.0 to 9.5, a reducing agent and a detergent, wherein the reducing agent is selected from the group consisting of 2-mercaptoethanol, thiosulfate, tris-(2-carboxyethyl) phosphine (TCEP), dithiothreitol, dithioerythritol, and the detergent is selected from the following group:

2-[4-(2,4,4-trimethylpentan-2-yl)phenoxy]ethanol, Polyoxyethylene (20) sorbitan monolaurate, Polyoxyethylene (80) sorbitan monooleate, Octylphenoxypolyethoxyethanol, Polyethylene glycol lauryl ether, an ethoxylated amine detergent, an alkylbenzene sulfonate detergent, and sodium dodecyl sulfate (SDS).

11. The method of claim 8, wherein the transport solution further comprising a Tris-HCL buffer having pH from 7.0 to 9.5 at a concentration of 50 mM to 150 mM.

12. The method of claim 1, wherein the pathogen is SARS-CoV-2.

13. The method of claim 1, wherein the activating solution comprises a Tris-HCL buffer having pH from 6.8 to 8.2 at a concentration of 5 mM to 20 mM; and the stabilized biological sample is diluted with the activating solution by a factor of 50 or by a factor of 100, or by a factor of 200.

14. The method of claim 1, wherein the amplification solution further comprising a reverse transcriptase enzyme.

* * * * *